United States Patent
Orr et al.

(10) Patent No.: US 11,099,632 B2
(45) Date of Patent: Aug. 24, 2021

(54) SYSTEMS AND METHODS FOR GUIDING AND MEASURING NECK AND SHOULDER PROTRACTION AND RETRACTION MOTIONS IN VIRTUAL/AUGMENTED REALITY

(71) Applicant: XR Health IL LTD, Tel Aviv (IL)

(72) Inventors: Eran Orr, Brookline, MA (US); Miki Levy, Misgav Dov (IL)

(73) Assignee: XR HEALTH IL LTD, Tel Aviv (IL)

( * ) Notice: Subject to any disclaimer, the term of this patent is extended or adjusted under 35 U.S.C. 154(b) by 0 days.

(21) Appl. No.: 16/506,404

(22) Filed: Jul. 9, 2019

(65) Prior Publication Data

US 2020/0012336 A1    Jan. 9, 2020

Related U.S. Application Data

(60) Provisional application No. 62/695,642, filed on Jul. 9, 2018.

(51) Int. Cl.
```
G06F 3/01      (2006.01)
G06T 19/00     (2011.01)
G06T 7/70      (2017.01)
G09B 5/02      (2006.01)
A61B 5/11      (2006.01)
A61B 5/00      (2006.01)
```

(52) U.S. Cl.
CPC .......... *G06F 3/011* (2013.01); *A61B 5/11* (2013.01); *A61B 5/486* (2013.01); *G06T 7/70* (2017.01); *G06T 19/006* (2013.01); *G09B 5/02* (2013.01); *A61B 2505/09* (2013.01); *A61B 2562/0219* (2013.01); *A61B 2562/0223* (2013.01)

(58) Field of Classification Search
None
See application file for complete search history.

(56) References Cited

U.S. PATENT DOCUMENTS

2012/0253241 A1    10/2012 Levital et al.
2014/0296750 A1    10/2014 Einav et al.

OTHER PUBLICATIONS

International Search Report and Written Opinion for International Application No. PCT/US19/41020 dated Oct. 8, 2019.

*Primary Examiner* — Peter Hoang
(74) *Attorney, Agent, or Firm* — Foley Hoag LLP; Erik A. Huestis; Robert Piston (57) ABSTRACT

A virtual/augmented reality-based system for guiding patients through rehabilitation exercises and providing real time feedback is disclosed. In various embodiments the system, methods, and computer program products relate to guiding and measuring neck and shoulder motion, specifically protraction and retraction motions. A virtual reality environment includes a fixed object having a guidance feature and a moveable object having a complementary shape to the guidance features. Whether the fixed object is in a complimentary orientation to the movable object is determined. When the fixed object is in a complimentary orientation with the movable shape, an indication is presented to the user to perform a motion. A plurality of sensors determines a plurality of measurements relating to the motion of the user. Whether the fixed object is in a complementary orientation with the movable object is determined based on the plurality of measurements.

20 Claims, 8 Drawing Sheets

SYSTEMS AND METHODS FOR GUIDING AND MEASURING NECK AND SHOULDER PROTRACTION AND RETRACTION MOTIONS IN VIRTUAL/AUGMENTED REALITY

CROSS-REFERENCE TO RELATED APPLICATIONS

This application claims the benefit of priority of U.S. Provisional Patent Application No. 62/695,642, filed Jul. 9, 2018, the contents of which are incorporated herein by reference in its entirety.

BACKGROUND

Embodiments of the present disclosure generally relate to guiding and measuring neck and shoulder motion, specifically protraction and retraction motions, in virtual reality (VR) or augmented reality (AR) environments.

BRIEF SUMMARY

Systems, methods, and computer program products of the present invention providing a virtual environment to the user via a virtual or augmented reality system. A method of the present disclosure includes providing a virtual reality environment providing a virtual environment to the user via the virtual or augmented reality system. The virtual reality environment includes a first 3D object fixed in space and the first 3D object has a first shape. The virtual reality environment includes a second 3D object fixed to the user and the second 3D object having a second shape that is complementary to the first shape. Whether the first shape is in a complimentary orientation to the second shape is determined. When the first shape is in a complimentary orientation with the second shape, the user is indicated to perform a motion via the virtual or augmented reality system. A plurality of sensors determine a plurality of measurements relating to the motion of the user. Whether the second 3D object is in the complementary orientation with the first 3D object is determined based on the plurality of measurements.

A system of the present disclosure includes a virtual or augmented reality display adapted to display a virtual environment to a user, a plurality of sensors coupled to the user, and a computing node including a computer readable storage medium having program instructions embodied therewith. The program instructions are executable by a processor of the computing node to cause the processor to perform a method including providing a virtual reality environment providing a virtual environment to the user via the virtual or augmented reality system. The virtual reality environment includes a first 3D object fixed in space and the first 3D object has a first shape. The virtual reality environment includes a second 3D object fixed to the user and the second 3D object having a second shape that is complementary to the first shape. Whether the first shape is in a complimentary orientation to the second shape is determined. When the first shape is in a complimentary orientation with the second shape, the user is indicated to perform a motion via the virtual or augmented reality system. A plurality of sensors determine a plurality of measurements relating to the motion of the user. Whether the second 3D object is in the complementary orientation with the first 3D object is determined based on the plurality of measurements.

A computer program product of the present disclosure includes a computer readable storage medium having program instructions embodied therewith. The program instructions are executable by a processor to cause the processor to perform a method including providing a virtual reality environment providing a virtual environment to the user via the virtual or augmented reality system. The virtual reality environment includes a first 3D object fixed in space and the first 3D object has a first shape. The virtual reality environment includes a second 3D object fixed to the user and the second 3D object having a second shape that is complementary to the first shape. Whether the first shape is in a complimentary orientation to the second shape is determined. When the first shape is in a complimentary orientation with the second shape, the user is indicated to perform a motion via the virtual or augmented reality system. A plurality of sensors determine a plurality of measurements relating to the motion of the user. Whether the second 3D object is in the complementary orientation with the first 3D object is determined based on the plurality of measurements.

DETAILED DESCRIPTION

In physical medicine and rehabilitation, also called physical therapy or physiotherapy, patients work with a physical therapist to enhance and/or restore their functional ability (and quality of life) after suffering physical impairment or disability. In general, a program of physical therapy is based on an individual's history and the results of a physical examination to arrive at a diagnosis. A given physical therapy program may integrate assistance with specific exercises, manual therapy and manipulation, mechanical devices such as traction, education, physical agents such as heat, cold, electricity, sound waves, radiation, assistive devices, prostheses, orthoses and other interventions. Physical therapy may also be prescribed as a preventative measure to prevent the loss of mobility before it occurs by developing fitness and wellness-oriented programs for healthier and more active lifestyles. This may include providing therapeutic treatment where movement and function are threatened by aging, injury, disease or environmental factors. During physical therapy, patients may perform a number of exercises focused on rehabilitating a particular injured area of the body (e.g., the neck and/or limbs after a spinal injury) or part of the body that has undergone a surgical procedure (e.g., carpal tunnel surgery, knee replacement surgery, shoulder replacement surgery, hip replacement surgery, muscle/ligament repair, spinal fusion, etc.).

As an example, individuals suffer from neck pain or need to perform neck exercises for various reasons. For example, people who have been involved in a motor vehicle accident or have suffered an injury while playing contact sports are prone to develop a whiplash associated disorder (WAD), a condition resulting from cervical acceleration-deceleration (CAD). It will be appreciated that this is just one of many potential injuries that may result in neck injury or pain necessitating rehabilitation.

The majority of people who suffer from non-specific neck pain (NSNP) may have experienced symptoms associated with WAD or have an undiagnosed cervical herniated disc. For this population, the recommended treatment regimen often includes a variety of exercises promoting neck movement and other functional activity training, leading to improved rehabilitation.

For patients that may not have access to nearby physical therapy, home training may have limitations. With no direct guidance from the clinician, the patient has no immediate feedback to confirm correct performance of required exercises. Lack of such guidance and supervision often leads to even lower adherence. As a result, the pain of an initial sensed condition may persist or even worsen—leading to other required medical interventions that could have been prevented, thus also increasing associated costs of the initial condition.

A physical therapist generally has to demonstrate the desired motions for each exercise to a patient undergoing the therapy and also correct the patient if the patient deviates from the proper exercise motion. For a patient to receive real-time feedback on the exercises, the therapist must be present to ensure the exercises are performed correctly and provide the feedback. Improperly performing rehabilitation exercises are dangerous to a patient because the patient may not heal correctly or may further damage the injured area.

Moreover, there is no bio-feedback loop for a patient undergoing rehabilitation therapy, that is, there is no way for the patient to automatically visualize his/her motion and to correct the motion if the motion is wrong.

Accordingly, a need exists for a system and method that provides real-time guidance and feedback regarding the accuracy and quality of physical therapy exercise motions (e.g., protraction and retraction), and can measure the length of the motion in real time thereby enabling bio-feedback, quantification, and progress control of the rehabilitation process.

The VR/AR technology according to various embodiments provides a fully immersive environment that enables measurement and guidance of motion performed by a patient/user. For example, the VR/AR technology may allow measurement and guidance of protraction and retraction motions of the neck and shoulders. Within this VR/AR environment, one or more virtual three-dimensional fixed objects (e.g., one, two three, four, five, six, etc.) are provided such that the fixed object(s) are perceived as having length, width, and depth. Each of the three-dimensional fixed objects may have a particular defined shape (e.g., box, disk, sphere, cylinder) or may not have any defined shape (e.g., an amorphous shape). Each of the fixed objects may include one or more guidance features configured to guide the motion of the patient/user as will be described in more detail below. The guidance features may be, for example, a longitudinal cylindrical groove extending along a surface of the fixed object. The guidance feature may also include one or more holes in the fixed object and/or one or more targets on the fixed object.

The VR/AR environment also includes one or more virtual three-dimensional moveable objects that are each associated with a body part of the patient/user for motion tracking. In various embodiments, the moveable object in the VR/AR environment is linked to a device that is attached to the patient's/user's body for which motion is to be tracked. The device may interact with the VR/AR technology (e.g., with sensors) by providing positional information to the VR/AR technology for moving the moveable objects in the VR/AR environment. In various embodiments, each of the moveable objects is associated with, e.g., one or both shoulders, the neck, one or both arms, one or both legs, and/or any other suitable body part. In various embodiments, the moveable objects have a particular shape in the VR/AR environment that is complementary to the one or more guidance features of the fixed object(s) described above.

As used herein, complementary, a complementary relationship, or complementary orientation (collectively, "complementary") is where one shape (e.g., the fixed object) has a groove that corresponds to at least a part of another shape (e.g., the moveable object) to assist in the guidance of a user's motion during a rehabilitation exercise. In various embodiments, the fixed object may have a groove that is complementary to a part of the moveable object. In various embodiments, the moveable object may include a groove that is complementary to a part of the fixed object.

In an example, the fixed object may be a rectangular block having a guidance feature in the form of a semi-cylindrical groove extending longitudinally along the length of a surface while the moveable object associated with a shoulder of the patient/user is a spherical shape that is complementary to the semi-cylindrical shape of the groove. In various embodiments, the guidance feature may include a convex and/or concave curvature. In various embodiments, the curvature of the fixed object may approximate (e.g., be equal to) the curvature of the movable object. In various embodiments, the movable object may include a convex and/or concave curvature that is complementary to the shape of the guidance feature. In this particular example, the spherical shape may have substantially the same radius as the radius of the semi-cylindrical groove thereby allowing the spherical shape to fit closely within the groove or otherwise match the shape of the groove. In other embodiments, the guidance feature may be a rectangular/box shape, triangular shape, pyramidal shape, conical shape, spherical shape, cylindrical shape, or any other suitable shape. In other embodiments, the guidance feature may be an embossed section instead of a grooved/engraved section. In other embodiments, the guidance feature need not be a groove or embossed as the fixed object itself may be a guidance feature (e.g., a disk-shaped target).

To initiate a rehabilitation session with a patient/user, the VR/AR technology may instruct the patient/user to position the one or more moveable objects in a complementary relationship with the one or more fixed objects. In the example above, the VR/AR technology may instruct a patient/user to position the movable object (e.g., spherical ball) in a complementary relationship with the guidance feature (e.g., longitudinal groove) of the fixed object. The VR/AR technology may instruct the patient/user to perform a sliding motion while keeping the spherical ball adjacent to the groove. In other embodiments, the VR/AR technology may instruct a user to motion towards a target.

The VR/AR technology may measure the length of protraction and/or retraction of the patient's/user's body in real time using positional coordinates of the moveable object determined from sensors in the VR/AR system. Sensors used in VR/AR are described in more detail below. Using the above example, the sensors may determine whether the spherical ball is aligned with the groove or if the patient/user positions the spherical ball away from the groove. In the event the spherical ball moves away from or out of the groove, the VR/AR technology may provide feedback to the user (e.g., through a textual or symbolic warning) that the motion is incorrect and provide instruction as to how to correct the motion (e.g., by placing the spherical ball back into the groove).

The VR/AR technology may provide instruction through the form of directional arrows in the VR/AR environment. The directional arrows may instruct a patient/user to move in a particular direction or may provide active feedback for performing a particular motion or exercise. In various embodiments, the VR/AR environment may include a feedback mechanism in the form of arrows. For example, the VR/AR environment may include two feedback arrows (e.g., up and down), four feedback arrows (up, down, left, and right), or six feedback arrows (up, down, left, right, forward, and backward) for providing feedback regarding the motion of the patient/user. Using the above example, if the patient/user should move the virtual spherical ball up to properly execute an exercise, the up arrow would highlight while the other arrow(s) would not be highlighted. In another example, if the patient/user is performing the exercise correctly, no arrow may be highlighted and/or an indication of compliance may be shown to the user. In other embodiments, certain features/areas in the VR/AR environment may be highlighted or a color may be changed to indicate that the motion is incorrect. In these embodiments, the patient may be instructed to move in the direction that reduces the highlighted/colored area.

This VR/AR platform thus enables accurate measurements of patient/user motion during therapy sessions and real-time feedback regarding compliance with the motions of a particular therapeutic exercise.

It will be appreciated that a variety of virtual and augmented reality devices are known in the art. For example, various head-mounted displays providing either immersive video or video overlays are provided by various vendors. Some such devices integrate a smart phone within a headset, the smart phone providing computing and wireless communication resources for each virtual or augmented reality application. Some such devices connect via wired or wireless connection to an external computing node such as a personal computer. Yet other devices may include an integrated computing node, providing some or all of the computing and connectivity required for a given application.

Virtual or augmented reality displays may be coupled with a variety of motion sensors in order to track a user's motion within a virtual environment. Such motion tracking may be used to navigate within a virtual environment, to manipulate a user's avatar in the virtual environment, or to interact with other objects in the virtual environment. In some devices that integrate a smartphone, head tracking may be provided by sensors integrated in the smartphone, such as an orientation sensor, gyroscope, accelerometer, or geomagnetic field sensor. Sensors may be integrated in a headset, or may be held by a user, or attached to various body parts to provide detailed information on user positioning.

In various embodiments, a user is furnished with a VR or AR system. As noted above, a VR or AR system will generally have integrated motion sensors. In addition, additional motions sensors may be provided, for example to be handheld. This allows tracking of multiple patient attributes while they interact with a scene. In this way, systematic and reproducible scenarios may be used to assess the subject's function.

In various embodiments, the guidance feature of the fixed object may define a predetermined path. In various embodiments, the predetermined path may be selected based on a particular rehabilitation protocol. For example, a rehabilitation protocol for neck protraction and/or retraction may involve different motions (and thus have different predetermined paths) than a rehabilitation protocol for shoulder protraction and/or retraction. In various embodiments, the VR/AR system may compare a path defined by a plurality of recorded three-dimensional points of the motion of the movable object to the predetermined path of the rehabilitation protocol. In various embodiments, the system may indicate to the user whether or not they are complying with the rehabilitation protocol. For example, the VR/AR system may present a warning if the movable object is not in a complementary relationship with the guidance feature of the fixed object. In another example, the VR/AR system may determine whether the user followed the entire predetermined path of the rehabilitation protocol. In this example, the VR/AR system may instruct the user that the rehabilitation protocol is not complete when the user did not follow the entire path or may instruct the user that the rehabilitation protocol is complete if the predetermined path was followed (while the movable object is in a complementary orientation with the guidance feature).

In various embodiments, the VR/AR system may instruct a user to hold the movable object in a complementary relationship for a predetermined amount of time (which may be based on a rehabilitation protocol). In various embodiments, the VR/AR system may record the amount of time that the movable object is held in the particular position. In various embodiments, a difference is calculated between the predetermined amount of time and the recorded time. In various embodiments, the VR/AR system may notify the user of the elapsed time via, for example, a timer and/or a clock. In various embodiments, if the user does not hold the movable object in the particular position for at least the predetermined amount of time, the VR/AR system may notify the user that they did not complete the rehabilitation protocol. In various embodiments, if the user holds the movable object in the particular position for at least the predetermined amount of time, the VR/AR system may notify the user that they completed the rehabilitation protocol. In various embodiments, results of each rehabilitation session, exercises completed and/or not completed, and/or elapsed times, may be recorded in the particular patient's record within an EHR database.

Figure 1:
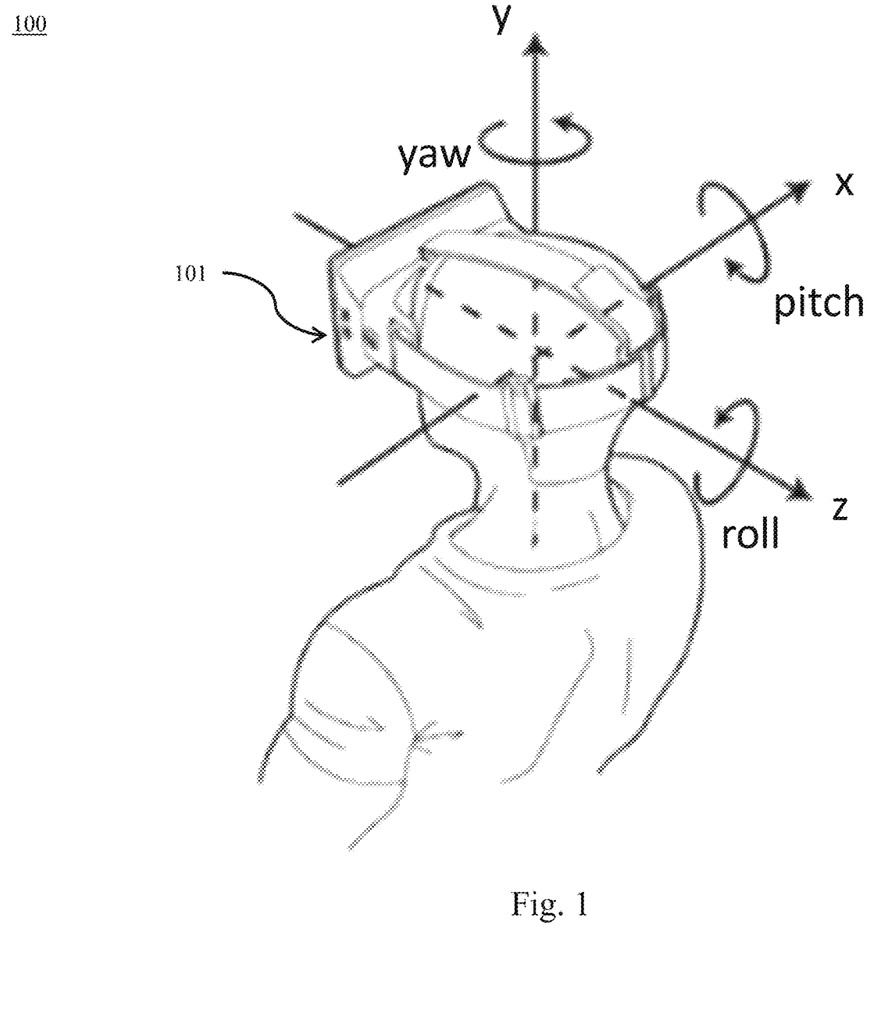
FIG. 1 illustrates an exemplary virtual reality headset according to embodiments of the present disclosure.

With reference now to FIG. 1, an exemplary virtual reality headset is illustrated according to embodiments of the present disclosure. In various embodiments, system 100 is used to collected data from motion sensors including hand sensors (not pictured), sensors included in headset 101, and additional sensors such as sensors placed on the body (e.g., torso, limbs, etc.) or a stereo camera. In some embodiments, data from these sensors is collected at a rate of up to about 150 Hz. As illustrated, data may be collected in six degrees of freedom: X axis translation—left/right; Y axis translation—up/down/height; Z axis translation forward/backward; P—pitch; R—roll; Y—yaw. As set out herein, this data may be used to track a user's overall motion to facilitate interaction with a virtual environment and to evaluate their performance. Pitch/Roll/Yaw may be calculated in Euler angles.

Figure 2:
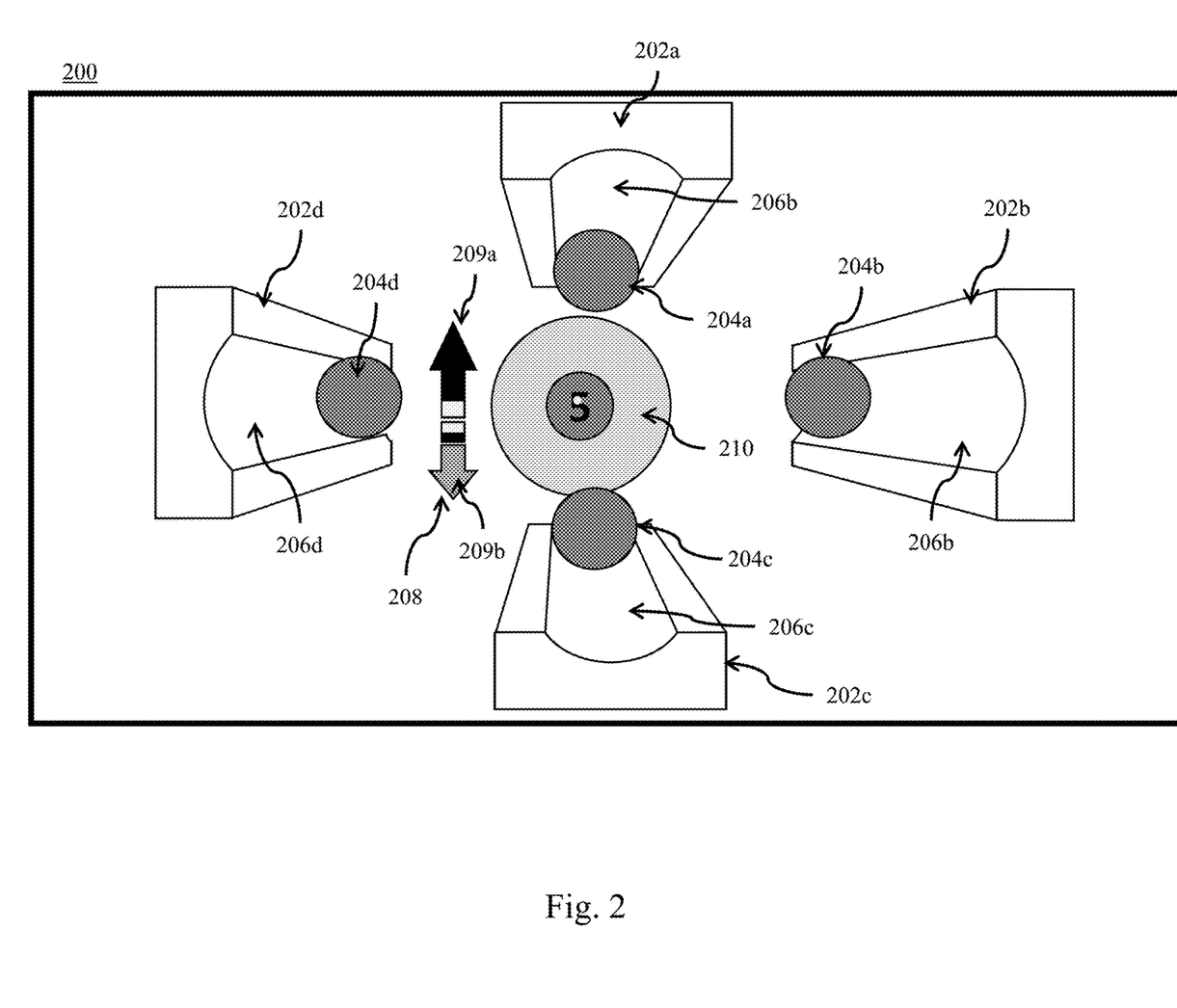
FIG. 2 illustrates an exemplary VR environment having fixed objects and moveable objects for guiding a patient/user through an exercise and providing real time feedback to the patient/user according to embodiments of the present disclosure.

FIG. 2 illustrates an exemplary VR environment 200 having fixed objects 202a-202d and moveable objects 204a-204d for guiding a patient/user through an exercise and providing real time feedback to the patient/user. In particular, the fixed objects 202a-202d are generally shaped as four rectangular blocks having guidance features 206a-206d on a surface in the form of semi-cylindrical cut-outs. In various embodiments, the fixed objects may have any suitable three-dimensional shape. For example, a fixed object may have a "puzzle piece" shape that fits into a corresponding moveable object in a specific way. The moveable objects 204a-204d are generally shaped as spheres having substantially the same radius as the guidance features 206a-206d of the fixed objects 202a-202d. The VR environment 200 further includes a feedback mechanism 208 to thereby provide real time feedback to the patient/user. The feedback mechanism 208 includes a forward arrow 209a and a backward arrow 209b that may be used by the VR environment 200 to indicate to the patient/user a specific direction/motion in which to move, e.g., protraction or retraction. In various embodiments, the feedback mechanism 208 may indicate the direction that the patient should move their body.

In an example, the VR environment 200 may highlight the forward arrow 209a of the feedback mechanism if the patient/user is to move their body in a forward direction so that a moveable object 204a-204d engages the corresponding fixed object 202a-202d in the guidance feature 206a-206d as described above. In various embodiments, highlighting may be achieved by coloring the forward arrow 209a or backward arrow 209b. In various embodiments, highlighting may be performed by increasing the size of the particular arrow and/or decreasing the size of the other arrow.

In various embodiments, the VR environment 200 may include a target 210 to aid the patient in performing a motion. For example, the patient may be instructed to aim at the target 210 to increase the likelihood that the patient performs the motion correctly. In various embodiments, the target 210 may be used to measure the rate of accuracy of the user motion where the user is instructed to aim at the target 210 (or a specific portion of the target, e.g., bullseye). Measurements of the accuracy of the patient motion may be used to determine the quality of the motions performed. For example, a patient who hits the bullseye of the target 210 may have a high accuracy score indicating high quality motions.

In various embodiments, two or more (e.g., all four) movable objects 204a-204d may be associated with a single body part of the user (e.g., the neck, shoulder, hand, foot, etc.). In this embodiment, the user may be required to align the movable objects 204a-204d with the respective guidance features 206a-206d of the fixed objects 202a-202d to initiate the rehabilitation session. In various embodiments, real-time feedback may be delivered to the user via the feedback mechanism 208 (e.g., up, down, left, and/or right arrows). In various embodiments, the real-time feedback may include instructions to complete the rehabilitation protocol, for example, to move the movable objects 204a-204d forward towards the target 210. In various embodiments, the real-time feedback may include a direction to move the one or more movable objects 204a-204d to put the one or more movable objects 204a-204d in a complementary orientation with the guidance features 206a-206d.

Figure 3:
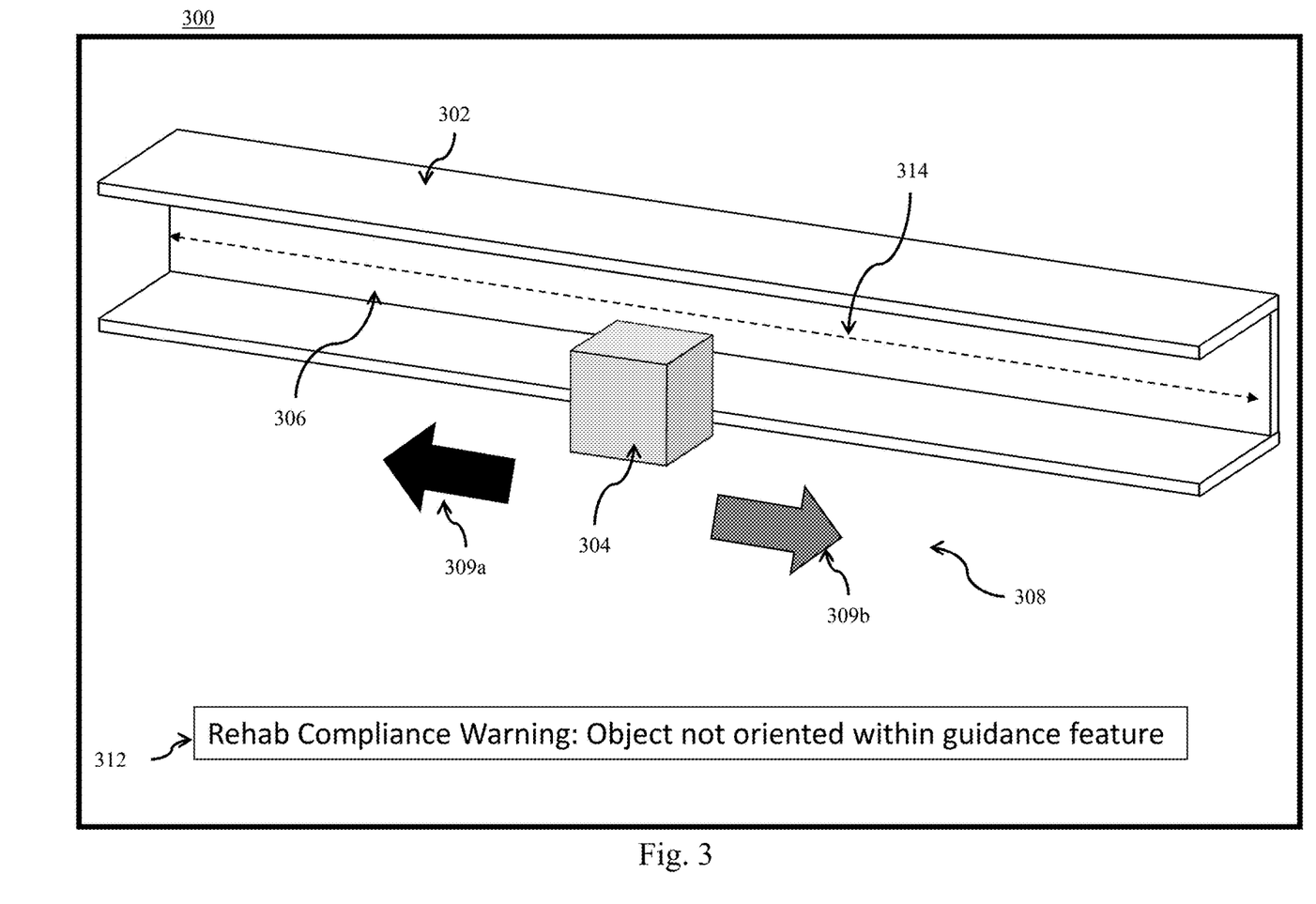
FIG. 3 illustrates an exemplary VR environment having a fixed object and a moveable object for guiding a patient/user through an exercise and providing real time feedback to the patient/user according to embodiments of the present disclosure.

FIG. 3 illustrates an exemplary VR environment 300 having a fixed object 302 and a moveable object 304 for guiding a patient/user through an exercise and providing real time feedback to the patient/user according to embodiments of the present disclosure. In this embodiment, the fixed object 302 is shaped as a beam having a guidance feature 306 in the form of a cubic cut-out along the length of the beam thereby creating a U-shaped beam. The moveable object 304 is generally shaped as a cube having substantially the same side length as the guidance feature 306 of the fixed object 302 (e.g., the movable object 304 has a complementary shape to the cubic cut-out). Similar to the VR environment in FIG. 2, the VR environment 300 further includes a feedback mechanism 308 to thereby provide real time feedback to the patient/user. The feedback mechanism 308 includes a left arrow 309a and a right arrow 309b that may be used by the VR environment 300 to indicate to the patient/user a specific direction/motion in which to move a body part (e.g., hand, foot, neck, shoulder, etc.) associated with the movable object 304. In FIG. 3, the left arrow 309a is highlighted (while right arrow 309b is not highlighted) indicating that the user should move the movable object 304 to the left once the movable object 304 is placed in a complementary orientation with the fixed object 302.

As shown in FIG. 3, because the movable object 304 (corresponding to a body part of the user) is not in a complementary orientation with the guidance feature 306 of the fixed object 302, an indication 312 is presented to the user, e.g., to inform the user that they are not in compliance with a rehabilitation protocol. In particular, the indication 312 is a message notifying the user that the movable object 304 is not in a complimentary orientation with the guidance feature 306. In various embodiments, any suitable indication may be implemented to notify the user that they are not complying with a rehabilitation protocol, such as, for example, one or more colors (red, yellow, and/or green), emojis, highlighting, and/or text overlay.

In various embodiments, the one or more arrows 309a, 309b may indicate a particular direction of motion of the user to thereby provide the user with visual feedback of the direction that the movable object is traveling in the VR environment. For example, when the user begins to move the movable object 304 to the left, the arrow 309a will be highlighted (and any highlighting on arrow 309b will disappear). In this example, when the user begins to move the movable object 304 to the right, the arrow 309b will be highlighted (and any highlighting on arrow 309a will disappear).

In various embodiments, the guidance feature 306 of the fixed object 302 defines a path 314 in which the movable object 304 may travel when in a complementary orientation with the guidance feature 306. In various embodiments, a rehabilitation protocol may include a predetermined path provided to the VR environment via, e.g., an EHR database. In various embodiments, the VR environment may collect three-dimensional positional data points of the movable object that define a path and determine a difference between the path traveled by the movable object and the predetermined path to assess compliance with the rehabilitation protocol. In various embodiments, if the difference between the path of the movable object 304 and the predetermined path is greater than or equal to a predetermined value, the VR environment 300 may indicate to the user that they are not in compliance with the rehabilitation protocol. In various embodiments, if the difference between the path of the movable object 304 and the predetermined path is less than a predetermined value, the VR environment 300 may indicate to the user that they are in compliance with the rehabilitation protocol and/or that the rehabilitation protocol is complete.

Figure 4:
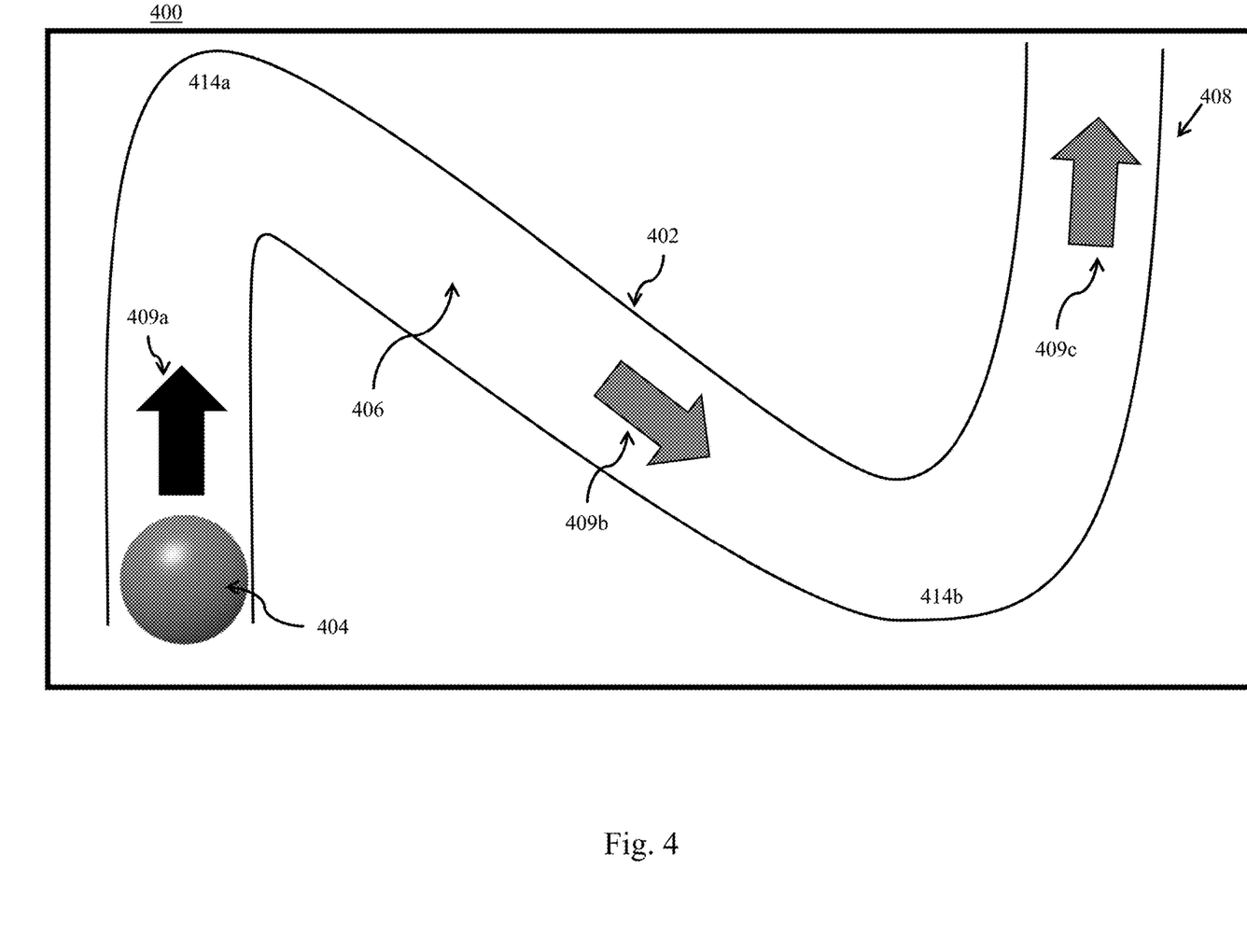
FIG. 4 illustrates an exemplary VR environment having a fixed object and a moveable object for guiding a patient/user through an exercise and providing real time feedback to the patient/user according to embodiments of the present disclosure.

FIG. 4 illustrates an exemplary VR environment 400 having a fixed object 402 and a moveable object 404 for guiding a patient/user through an exercise and providing real time feedback to the patient/user according to embodiments of the present disclosure. In this embodiment, the fixed object 402 is shaped as a winding object having multiple curves 414a, 414b. In various embodiments, the fixed object 402 may include a single curve. In this embodiment, the movable object 404 is spherical where the diameter substantially matches the dimensions of the guidance feature 406 of the fixed object 402. Similar to the VR environments described above, the VR environment 400 further includes a feedback mechanism 408 to thereby provide real time feedback to the patient/user. The feedback mechanism 408 includes arrows 409a, 409b, and 409c along the guidance feature 406 that may be used by the VR environment 400 to indicate to the patient/user a specific direction/motion in which to move a body part (e.g., hand, foot, neck, shoulder, etc.) associated with the movable object 404. In FIG. 4, the first arrow 409a closest to the starting point is highlighted (while arrows 409b and 409c are not highlighted) indicating that the user should move the movable object 404 along the winding guidance feature 406 once the movable object 404 is placed in a complementary orientation with the fixed object 402.

In various embodiments, as the user moves the movable object 404 along the curved guidance feature 406 of the fixed object 402, the next arrow 409b may be highlighted. For example, when the first arrow 409b is passed by the movable object 404 (due to the motion of the user while the movable object is in a complementary orientation with the guidance feature of the fixed object), the highlighting of the first arrow 409a may disappear and the second arrow 409b may be highlighted. Similarly, when the second arrow 409b is passed, the highlighting on the second arrow 409b may disappear and the third arrow 409c may be highlighted. In various embodiments, the arrows 409a-409c may maintain the highlighting as the movable object 404 passes each arrow.

Figure 5:
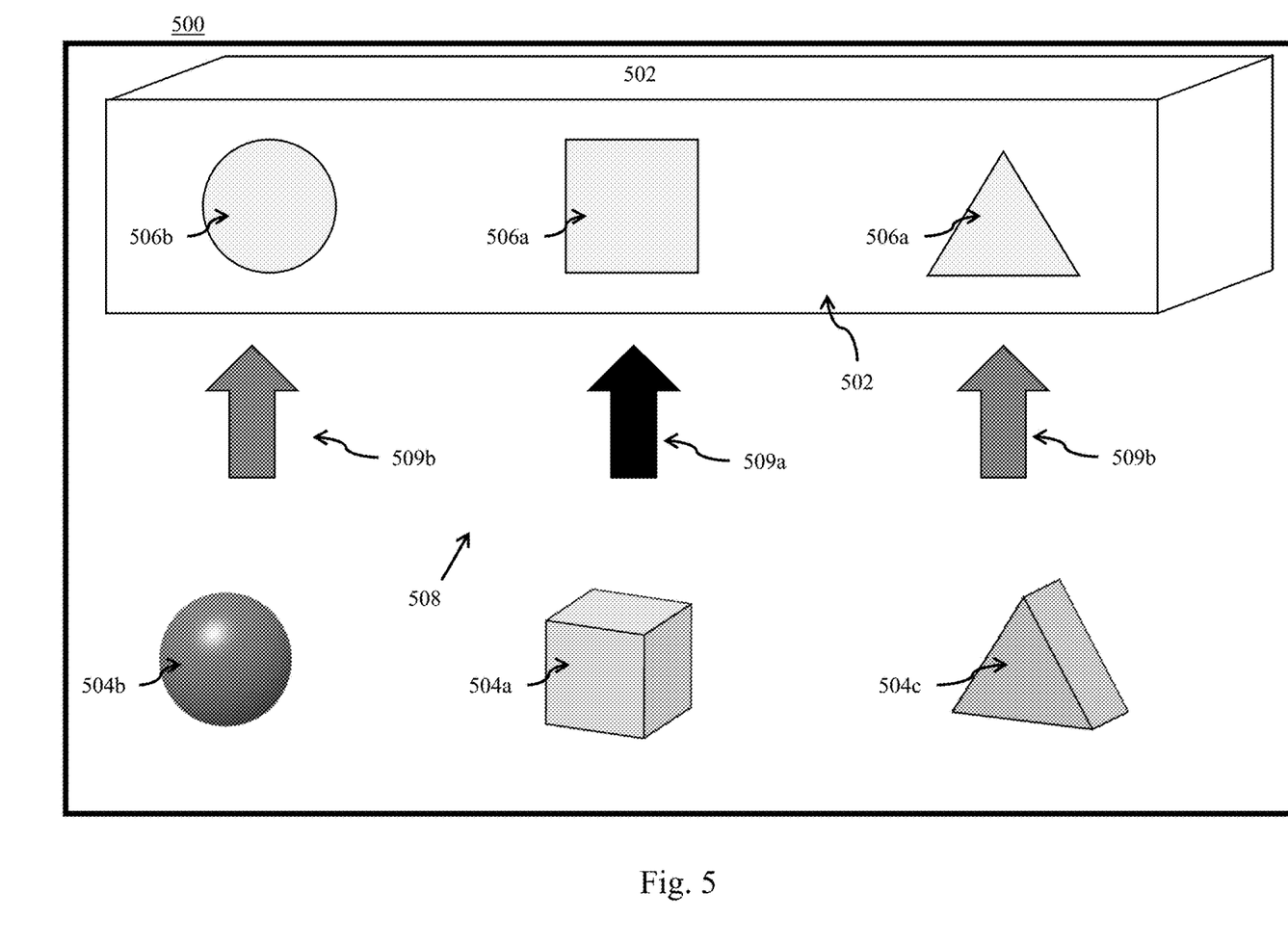
FIG. 5 illustrates an exemplary VR environment having a fixed object and moveable objects for guiding a patient/user through an exercise and providing real time feedback to the patient/user according to embodiments of the present disclosure.

FIG. 5 illustrates an exemplary VR environment 500 having a fixed object 502 and moveable objects 504a-504c for guiding a patient/user through an exercise and providing real time feedback to the patient/user according to embodiments of the present disclosure. In this embodiment, the VR environment 500 includes guidance features 506a-506c that specifically correspond to a particular movable object 504a-504c. For example, the guidance feature 506a is square in shape and therefor has a complementary orientation to the cubic movable object 504a. Similarly, the guidance feature 506b is circular in shape and therefor has a complementary orientation to the spherical movable object 504b while the guidance feature 506c is triangular in shape and therefor has a complementary orientation to the triangular movable object 504c.

Similar to the embodiments above, the VR environment 500 includes a feedback mechanism 508 that includes three arrows 509a-509c. In various embodiments, each arrow 509a-509c may be used to indicate to the patient which movable object 504a-504c to put in a complementary orientation with its respective guidance feature 506a-506c. For example, in FIG. 5, the first arrow 509a is highlighted thereby indicating to the user that the first movable object 509a should be placed in a complementary orientation with the square-shaped guidance feature 506a. In this example, the other two arrows 509b, 509c are not highlighted while the first arrow 509a is highlighted. In various embodiments, two or more arrows 509a-509c may be highlighted at the same time. In various embodiments, the arrows 509a-509c may be highlighted one at a time (e.g., sequentially) after a predetermined amount of time.

In various embodiments, the user may be instructed to hold one or more of the movable objects 509a-509c in a complementary orientation with the respective guidance feature(s) 506a-506c for a predetermined amount of time. In various embodiments, the VR environment may record the amount of time that the user holds the movable object 504a-504c in the complementary orientation with its respective guidance feature 506a-506c. In various embodiments, the VR environment 500 may present the user with a timer and/or clock so that the user may be aware of how long the movable object 504a-504c should be held in the complementary orientation. In various embodiments, the VR environment 500 may determine a compliance metric based on the recorded time. In various embodiments, the recorded time may be compared to the predetermined time to determine a difference. In various embodiments, if the difference is greater than a predetermined threshold, the user may be notified that the rehabilitation protocol is not complete. In various embodiments, if the difference is less than a predetermined threshold, the user may be notified that the rehabilitation protocol is complete.

Figure 6:
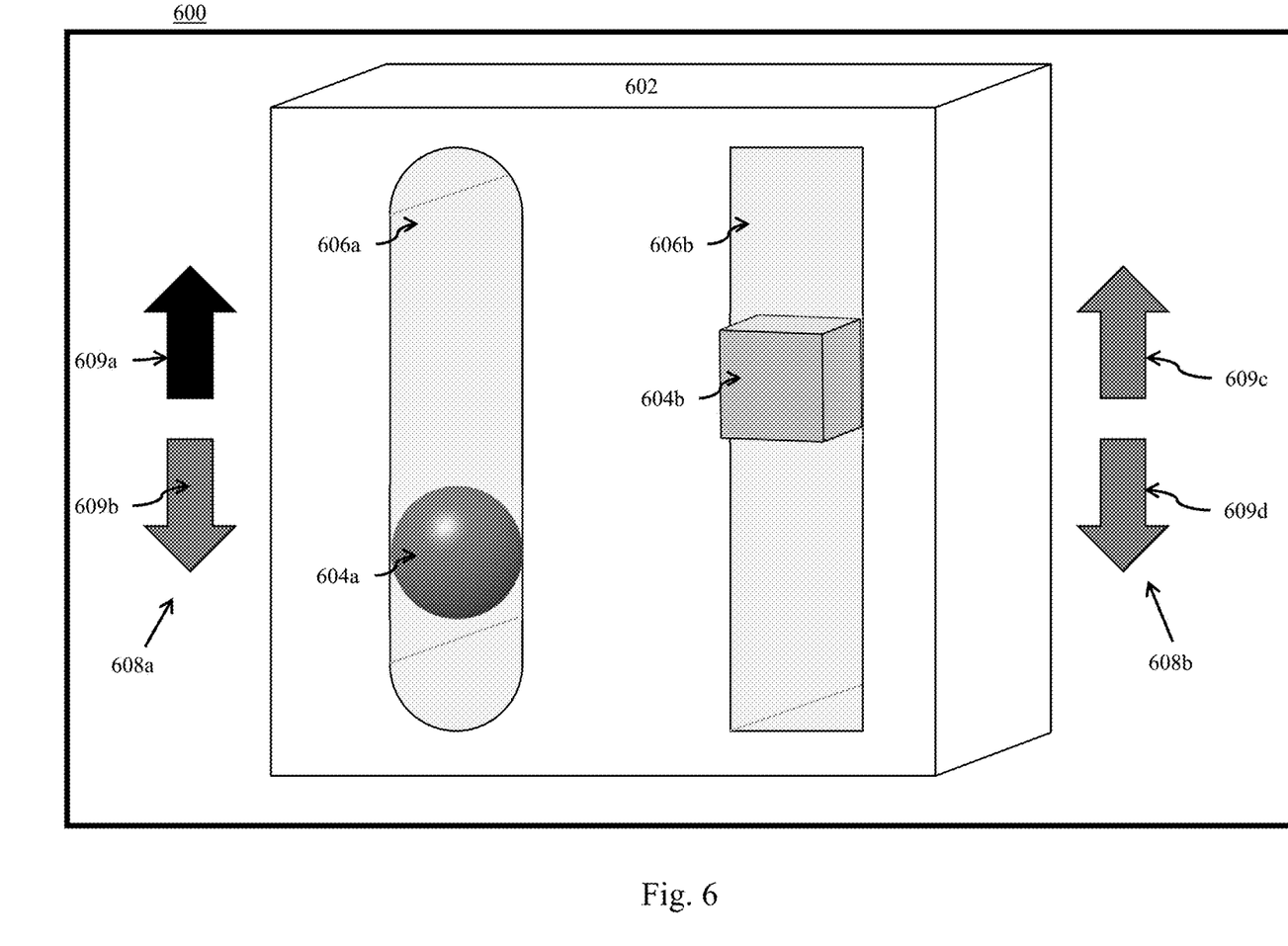
FIG. 6 illustrates an exemplary VR environment having a fixed object and moveable objects for guiding a patient/user through an exercise and providing real time feedback to the patient/user according to embodiments of the present disclosure.

FIG. 6 illustrates an exemplary VR environment 600 having a fixed object 602 and moveable objects 604a, 604b for guiding a patient/user through an exercise and providing real time feedback to the patient/user according to embodiments of the present disclosure. The fixed object 602 includes a guidance feature 606a that is a slot with arcuate ends and a guidance feature 606b that is a slot with square ends. Due to the arcuate shape of the ends of the guidance feature 606a, the first movable object 604a is capable of a complementary relationship with the guidance feature 606a throughout the entire length of the guidance feature 606a. Similarly, due to the square shape of the ends of the guidance feature 606b, the second movable object 604b is capable of a complementary relationship with the guidance feature 606b throughout the entire length of the guidance feature 606b.

The VR environment 600 further includes a first feedback mechanism 608a associated with the first movable object 604a and a second feedback mechanism 608b associated with the second movable object 604b. The first feedback mechanism 608a includes arrows 609a, 609b and the second feedback mechanism 608b includes arrows 609c, 609d. In FIG. 6, arrow 609a is highlighted to indicate to the user to move the first movable object 604a in the upward direction while the movable object 604a is in a complementary relationship with the guidance feature 606a. In various embodiments, an arrow from both feedback mechanisms 608a, 608b may be highlighted at the same time to indicate to the user that both movable objects 604a, 604b should be put in a complementary relationship with the respective guidance features 606a, 606b and moved in the indicated direction. In various embodiments, based on the rehabilitation protocol, the user may be instructed to move one or more of the movable objects 604a, 604b in the direction(s) indicated by the feedback mechanism(s) 608a, 608b. In various embodiments, the user may be instructed to hold one or more movable object 604a, 604b at a particular location within the guidance feature(s) 606a, 606b for a predetermined amount of time. The predetermined amount of time may be based on the particular rehabilitation protocol and may be any suitable amount of time as is known in the art.

Figure 7:
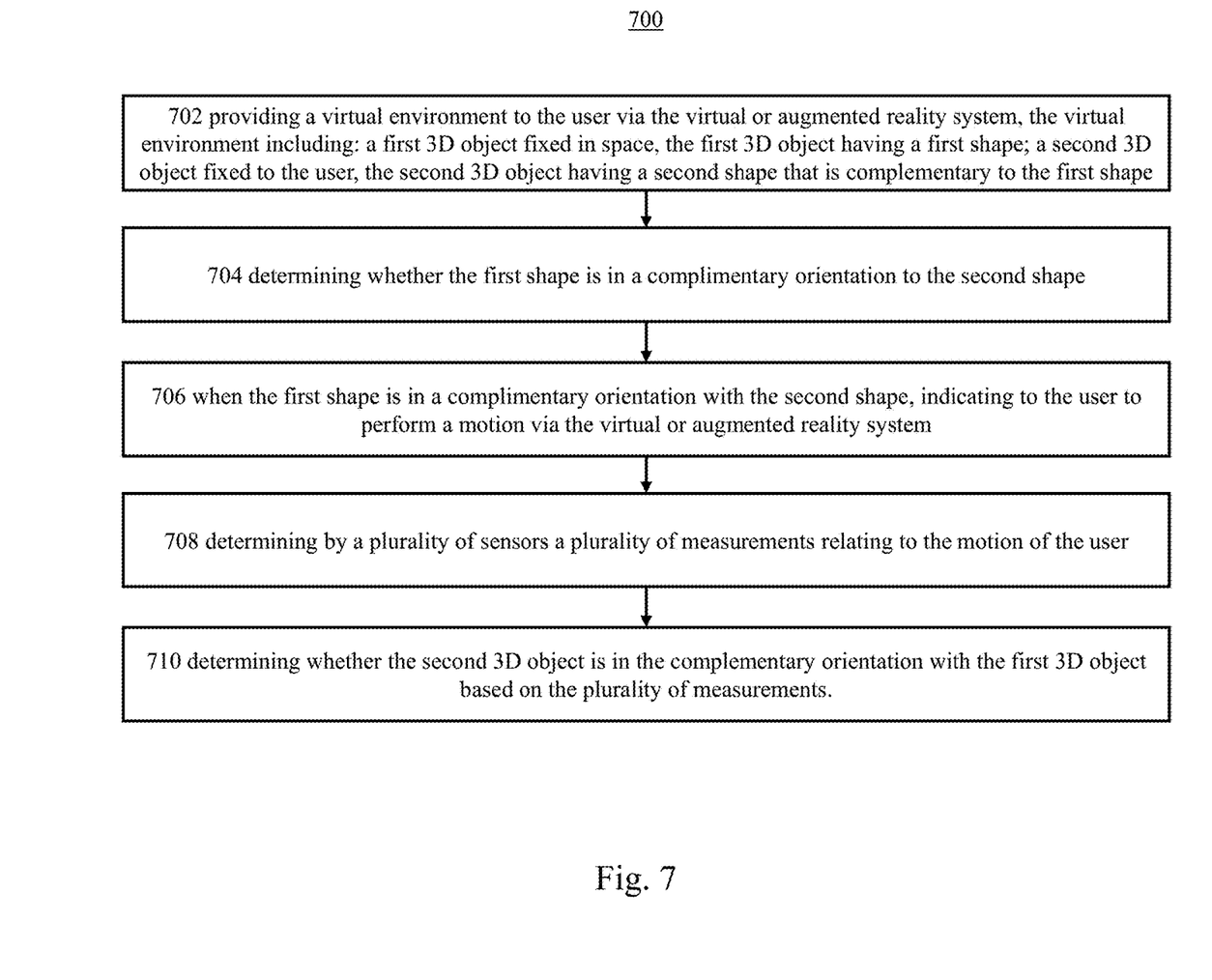
FIG. 7 is a flow chart illustrating an exemplary method for guiding a patient/user through an exercise and providing real time feedback to the patient/user.

FIG. 7 illustrates a flowchart for a method for guiding a patient/user through an exercise and providing real time feedback to the patient/user. At 702, the method includes providing a virtual environment to the user via the virtual or augmented reality system. The virtual environment includes a first 3D object fixed in space, the first 3D object having a first shape, and a second 3D object fixed to the user, the second 3D object having a second shape that is complementary to the first shape. At 704, the method includes determining whether the first shape is in a complimentary orientation to the second shape. At 706, the method includes, when the first shape is in a complimentary orientation with the second shape, indicating to the user to perform a motion via the virtual or augmented reality system. At 708, the method includes determining by a plurality of sensors a plurality of measurements relating to the motion of the user. At 710, the method includes determining whether the second 3D object is in the complementary orientation with the first 3D object based on the plurality of measurements.

In various embodiments, off the shelf VR systems are optionally used with additional external compatible sensors to track various elements in multiple fields including, e.g., motion tracking, cognitive challenges, speech recognition, stability, facial expression recognition, and biofeedback.

Motion tracking can include, but is not limited to tracking of gait, stability, tremors, amplitude of motion, speed of motion, range of motion, and movement analysis (smoothness, rigidity, etc.).

Cognitive challenges can include, but is not limited to reaction time, success rate in cognitive challenges, task fulfillment according to different kind of guidance (verbal, written, illustrated, etc.), understanding instructions, memory challenges, social interaction, and problem solving.

Speech Recognition can include, but is not limited to fluent speech, ability to imitate, and pronunciation.

Stability can include, but is not limited to postural sway.

Bio-Feedback can include, but is not limited to, Heart rate variability (HRV), Electrothermal activity (EDA), Galvanic skin response (GSR), Electroencephalography (EEG), Electromyography (EMG), Eye tracking, Electrooculography (EOG), Patient's range of motion (ROM), Patient's velocity performance, Patient's acceleration performance, and Patient's smoothness performance.

The following is a non-limiting example of guiding a patient/user through an exercise and providing real time feedback to the patient/use in accordance with various embodiments. A user wears a VR/AR headset (with optional tracking device on a particular body part) and enters a virtual environment. The user is provided a series of instructions and/or demonstrations regarding how to perform an exercise as a part of their rehabilitation plan. The user proceeds to perform the exercise and can visualize the moveable objects and fixed objects in the virtual environment used for guiding the exercise. The VR system may track the motion of the user and collect positional data of the user's body. While performing the exercise, the VR system may indicate which direction the user is to move their body by, for example, highlighting one or more arrows or areas within the three-dimensional object. In various embodiments, if the user deviates from the proper exercise motion, the virtual environment may provide an indication to the user that the motion is incorrect and provide real time feedback regarding how to correct the motion by, for example, highlighting one or more arrows or areas within the three-dimensional object.

Figure 8:
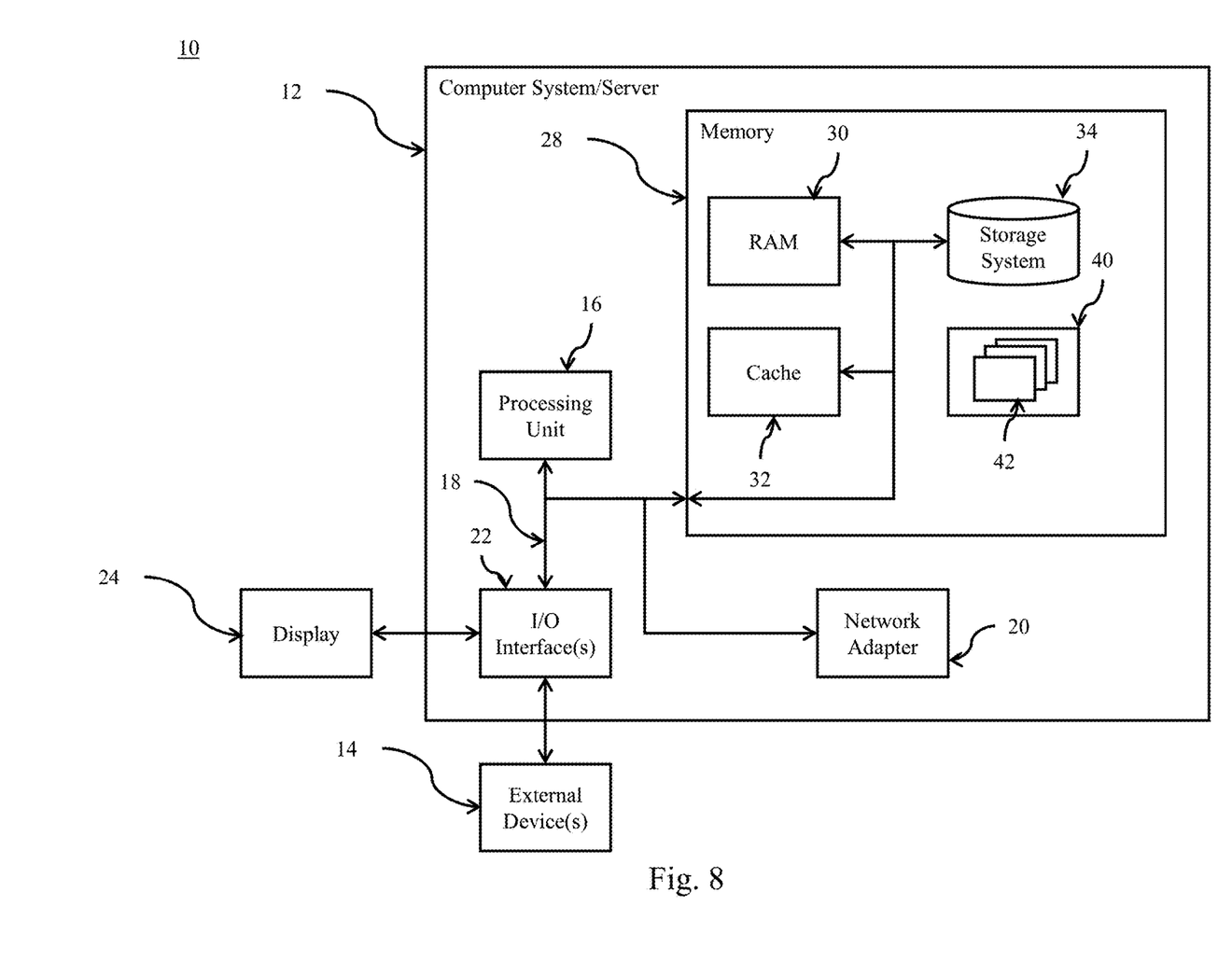
FIG. 8 depicts an exemplary computing node according to embodiments of the present disclosure.

Referring now to FIG. 8, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
providing a virtual environment to the user via the virtual or augmented reality system, the virtual environment comprising:
a first 3D object fixed in space, the first 3D object having a first shape, and
a second 3D object fixed to the user, the second 3D object having a second shape that is complementary to the first shape;
determining whether the first shape is in a complimentary orientation to the second shape;
when the first shape is in a complimentary orientation with the second shape, indicating to the user to perform a motion via the virtual or augmented reality system;
determining by a plurality of sensors a plurality of measurements relating to the motion of the user; and
determining whether the second 3D object is in the complementary orientation with the first 3D object based on the plurality of measurements.

2. The method of claim 1, wherein the first 3D object defines a first path, and wherein the plurality of measurements define a second path.

3. The method of claim 2, wherein the first path and the second path each comprises a plurality of three-dimensional points.

4. The method of claim 2, wherein determining whether the second 3D object is in the complementary orientation with the first 3D object comprises determining a difference between the first path and the second path.

5. The method of claim 4, further comprising, when the difference is greater than a predetermined threshold, providing an indication to the user that the second 3D object is not in a complementary relationship with the first 3D object.

6. The method of claim 5, further comprising, when the difference is greater than a predetermined threshold, providing an indication to the user of a direction of motion to position the second 3D object back in the complementary relationship with the first 3D object.

7. The method of claim 5, further comprising, when the difference is greater than or equal to the predetermined threshold, providing an indication to the user that the second 3D object is in a complementary relationship with the first 3D object.

8. A system comprising:
a virtual or augmented reality display adapted to display a virtual environment to a user;
a plurality of sensors coupled to the user;
a computing node comprising a computer readable storage medium having program instructions embodied therewith, the program instructions executable by a processor of the computing node to cause the processor to perform a method comprising:
providing a virtual environment to the user via the virtual or augmented reality system, the virtual environment comprising:
a first 3D object fixed in space, the first 3D object having a first shape, and
a second 3D object fixed to the user, the second 3D object having a second shape that is complementary to the first shape;
determining whether the first shape is in a complimentary orientation to the second shape;
when the first shape is in a complimentary orientation with the second shape, indicating to the user to perform a motion via the virtual or augmented reality system;
determining by a plurality of sensors a plurality of measurements relating to the motion of the user; and
determining whether the second 3D object is in the complementary orientation with the first 3D object based on the plurality of measurements.

9. The system of claim 8, wherein the first 3D object defines a first path, and wherein the plurality of measurements define a second path.

10. The system of claim 9, wherein determining whether the second 3D object is in the complementary orientation with the first 3D object comprises determining a difference between the first path and the second path.

11. The system of claim 10, further comprising, when the difference is greater than a predetermined threshold, providing an indication to the user that the second 3D object is not in a complementary relationship with the first 3D object.

12. The system of claim 11, further comprising, when the difference is greater than a predetermined threshold, providing an indication to the user of a direction of motion to position the second 3D object back in the complementary relationship with the first 3D object.

13. The system of claim 11, further comprising, when the difference is greater than or equal to the predetermined threshold, providing an indication to the user that the second 3D object is in a complementary relationship with the first 3D object.

14. A computer program product comprising a computer readable storage medium having program instructions embodied therewith, the program instructions executable by a processor to cause the processor to perform a method comprising:
 providing a virtual environment to the user via the virtual or augmented reality system, the virtual environment comprising:
  a first 3D object fixed in space, the first 3D object having a first shape, and
  a second 3D object fixed to the user, the second 3D object having a second shape that is complementary to the first shape;
 determining whether the first shape is in a complimentary orientation to the second shape;
 when the first shape is in a complimentary orientation with the second shape, indicating to the user to perform a motion via the virtual or augmented reality system;
 determining by a plurality of sensors a plurality of measurements relating to the motion of the user; and
 determining whether the second 3D object is in the complementary orientation with the first 3D object based on the plurality of measurements.

15. The computer program product of claim 14, wherein the first 3D object defines a first path, and wherein the plurality of measurements define a second path.

16. The computer program product of claim 15, wherein the first path and the second path each comprises a plurality of three-dimensional points.

17. The computer program product of claim 16, wherein determining whether the second 3D object is in the complementary orientation with the first 3D object comprises determining a difference between the first path and the second path.

18. The computer program product of claim 17, further comprising, when the difference is greater than a predetermined threshold, providing an indication to the user that the second 3D object is not in a complementary relationship with the first 3D object.

19. The computer program product of claim 18, further comprising, when the difference is greater than a predetermined threshold, providing an indication to the user of a direction of motion to position the second 3D object back in the complementary relationship with the first 3D object.

20. The computer program product of claim 18, further comprising, when the difference is greater than or equal to the predetermined threshold, providing an indication to the user that the second 3D object is in a complementary relationship with the first 3D object.

* * * * *